United States Patent
Holyfield

(10) Patent No.: US 8,460,652 B2
(45) Date of Patent: *Jun. 11, 2013

(54) TOPICAL SKIN CARE FORMULATIONS

(71) Applicant: Louise Holyfield, Dallas, TX (US)

(72) Inventor: Louise Holyfield, Dallas, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 13/573,537

(22) Filed: Sep. 21, 2012

(65) Prior Publication Data

US 2013/0108604 A1      May 2, 2013

Related U.S. Application Data

(62) Division of application No. 12/284,398, filed on Sep. 22, 2008, now Pat. No. 8,314,154.

(51) Int. Cl.
*A61K 38/43*      (2006.01)

(52) U.S. Cl.
USPC ........................................................ 424/94.1

(58) Field of Classification Search
None
See application file for complete search history.

(56) References Cited

U.S. PATENT DOCUMENTS

2010/0076090 A1*   3/2010   Holyfield ...................... 514/690

* cited by examiner

*Primary Examiner* — Suzanne M Noakes
*Assistant Examiner* — Stephen Chong
(74) *Attorney, Agent, or Firm* — Gary C Honeycutt

(57) ABSTRACT

A topical anti-aging skin care formulation comprising an effective amount of a benzoquinone, such as CoQ10, plus a synergistic pair of stabilizers and a synergistic pair of whiteners. The stabilizers are octyl salicylate and octyl methoxycinnamate. The whiteners are titanium dioxide and zinc oxide. When proper amounts of these ingredients are used in an aqueous based emulsion formulation, the product will be initially white, and will remain white for an extended period of time.

4 Claims, No Drawings

TOPICAL SKIN CARE FORMULATIONS

This is a Division of application Ser. No. 12/284,398 filed Sep. 22, 2008.

FIELD OF THE INVENTION

This invention relates to chemical compositions, and more particularly to topical skin care formulations.

BACKGROUND OF THE INVENTION

People have been conscious of the need for skin care for thousands of years. For example, the ancient Romans, Greeks and Egyptians applied various natural products to their skin, including olive oil, honey, and sour milk for various reasons, including cleanliness, comfort, beauty, and protection against the sun. Since then, research has confirmed the benefits of using such natural products.

In recent decades, the demand for effective topical creams and lotions that both beautify and protect the skin from free radicals and stress oxidation increases annually. By 2010 it is estimated that $44.6 billion dollars will be spent annually on skin care products. We live in a society that admires healthy skin, because it is essential to beauty. More than ever before, we now understand that both females and males seek out anti-aging products that have the ability to improve their skin and fight against the visual signs of aging. Consumers are particularly interested in products that have added benefits such as antioxidants that fight free radicals that damage skin cells.

As we have learned more about the aging process, coenzyme Q10 and other ubiquinones have emerged as a powerful, potent and effective class of antioxidants, not only for use as dietary supplements, but also as effective ingredients in topical anti-aging skin care products, when used in effective amounts. U.S. Pat. No. 6,906,106, issued to L'Oreal on Jun. 14, 2005, discloses numerous topical anti-aging skin care formulations comprising ubiquinones and derivatives thereof, including CoQ10. The patent also lists thousands of useful known ingredients, and suggests hundreds of thousands of possible combinations thereof, as suitable additions to such formulations. The purposes of all these known ingredients are acknowledged by L'Oreal to be well-known. Examples include water, solvents, oils, emulsifiers, esters, paraffins, fatty alcohols, fatty acids, silicone oils, moisturizers, vitamins, minerals, whiteners, UV filters, flavonoids, and gelling agents.

U.S. Pat. No. 7,150,876, issued to Merck on Dec. 19, 2006, discloses the stabilization of thousands of poly-unsaturated aromatic compounds found in hundreds of household products and health care formulations. The list of compounds to be stabilized includes ubiquinones, and the list of stabilizers appears to include most of the known sunscreens. But there is no disclosure of which sunscreens work best for stabilizing ubiquinones.

SUMMARY OF THE INVENTION

CoQ10 is known and readily recognized worldwide as being one of the most potent and effective antioxidants in the fight against the visual signs of aging skin. However, aqueous based emulsion products containing CoQ10 are usually yellow in color, and tend to become much darker in color during the normal shelf life of the product. Despite the numerous benefits of this powerful and effective antioxidant, consumers are not receptive to a product that is not white, and/or not color-stable.

This invention provides a topical anti-aging formulation for the skin, comprising an effective amount (at least 2% by wt.) of a benzoquinone, such as CoQ10, plus a synergistic pair of whiteners and a synergistic pair of stabilizers to prevent discoloration and degradation. The whiteners are titanium dioxide and zinc oxide. The stabilizers are octyl salicylate and octyl methoxycinnamate. When proper amounts of these ingredients are used in an aqueous based emulsion formulation, the product will be white in color and will remain so, without significant degradation, for at least two years.

No single whitener is as effective as the combination of at least 0.1 to 1.0% by wt. titanium dioxide and at least 0.005 to 1.0% zinc oxide. More whitener could be used, but it is not desirable or necessary. No single stabilizer is as effective as the combination of octyl salicylate, at least 1.0% by wt. and octyl methoxycinnamate, at least 1.0% by wt. More could be used, but it is not desirable or necessary.

EXAMPLES

A. 3% by wt. CoQ10
   2% by wt. octyl salicylate
   2% by wt. octyl methoxycinnamate
   0.25% by wt. titanium dioxide
   0.02% by wt. zinc oxide
   about 93% by wt. inactive ingredients and emulsifiers B. 4% by wt. CoQ10
   2.67% by wt. octyl salicylate
   2.67% by wt. octyl methoxycinnamate
   0.33% by wt. titanium dioxide
   0.03% by wt. zinc oxide
   about 90% by wt. inactive ingredients and emulsifiers C. 2% by wt. CoQ10
   1.33% by wt. octyl salicylate
   1.33% by wt. octyl methoxycinnamate
   0.167% by wt. titanium dioxide
   0.013% by wt. zinc oxide
   about 95% by wt. inactive ingredients and emulsifiers There are many well-known inactive ingredients and emulsifiers useful in the skin care formulations of the invention. For a suitable list of such ingredients, see U.S. Pat. No. 6,906,106, incorporated herein by reference. The usual methods for blending the ingredients are used to prepare the formulations of the invention. Examples of such methods are also disclosed in U.S. Pat. No. 6,906,106, incorporated herein by reference.

For purposes of this invention, the term "ubiquinones" includes all related compounds and derivatives thereof. For a suitable list of ubiquinones, related compounds and derivatives, see U.S. Pat. No. 6,906,106, incorporated herein by reference.

Still more ingredients for optional addition to the products of this invention include kakadu plum extract and acai berry extract, and others listed in U.S. patent application Ser. No. 11/624,985 filed Jan. 19, 2007 entitled "Compositions Comprising Kakadu Plum Extract or Acai Berry Extract", the entire disclosure of which is incorporated herein by reference.

The invention claimed is:

1. A method for extending the shelf-life of a white anti-aging skin care formulation containing at least about 2 wt % of a benzoquinone, comprising the step of adding octyl salicylate and octyl methoxycinnamate to said formulation.

2. A method as in claim 1 wherein said benzoquinone is CoQ10.

3. A method as in claim 1 wherein said formulation includes titanium dioxide and zinc oxide.

4. A method as in claim 1 wherein said formulation includes:
- from 2.0 to 4.0 wt % CoQ10;
- from 0.1 to 1.0 wt % titanium dioxide;
- from 0.005 to 1.0 wt % zinc oxide;
- a white oil-in-water emulsion;
- and wherein the amount of added octyl salicylate is from 1.0 to 2.0 wt %; and
- the amount of added octyl methoxycinnamate is 1.0 to 2.0 wt %.

* * * * *